United States Patent [19]
Blanche et al.

[11] Patent Number: 5,591,614
[45] Date of Patent: Jan. 7, 1997

[54] PROCESS FOR THE ENZYMATIC PREPARATION OF MACROLACTONE

[75] Inventors: Francis Blanche; Denis Thibaut, both of Paris, France

[73] Assignee: Rhone-Poulenc Rorer, S.A., Antony, France

[21] Appl. No.: 417,445

[22] Filed: Apr. 5, 1995

Related U.S. Application Data

[63] Continuation of Ser. No. 119,229, filed as PCT/FR92/00270, Mar. 26, 1992 published as WO92/17491, Oct. 15, 1992, abandoned.

[30] Foreign Application Priority Data

Mar. 28, 1991 [FR] France .................................. 91 03779

[51] Int. Cl.$^6$ ..................................................... C12P 17/14
[52] U.S. Cl. ..................... 435/120; 435/119; 435/68.1; 435/886; 435/253.5
[58] Field of Search .................................. 435/120, 119, 435/68.1, 253.5, 886, 252.1

[56] References Cited

U.S. PATENT DOCUMENTS 3,137,640  6/1964  Watanabe .............................. 514/375

OTHER PUBLICATIONS

Goodfellow et al "The Biology of the Actinomycetes" 1984, p. 67–69.
Purvis et al, J. Am: Chem. Soc., 1989, vol. III, pp. 5931–5935.
Zeitschrift für. Allg. Mikrobiologie, vol. 22, 1982, pp. 155–160.

*Primary Examiner*—Irene Marx
*Attorney, Agent, or Firm*—Finnegan, Henderson, Farabow, Garrett & Dunner, L.L.P.

[57] ABSTRACT

This invention concerns a process for enzymatically preparing a compound of formula (1)

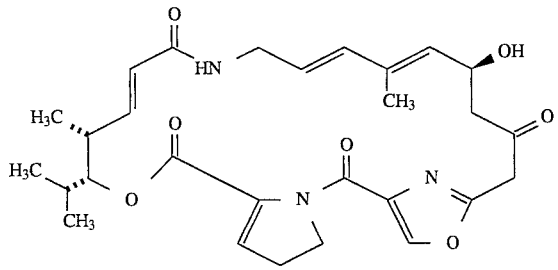

from the compound of formula (2)

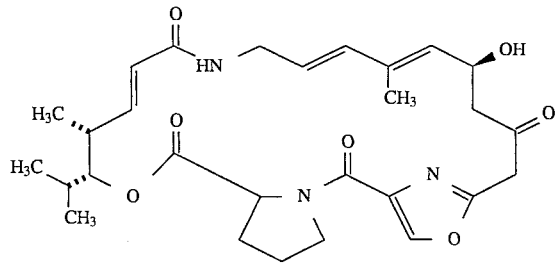

by way of a microorganism or an acellular preparation derived from this microorganism. The microorganism and acellular preparation oxidizes the 2–3 bond of the macrolactones' D-proline into dehydroproline.

8 Claims, 1 Drawing Sheet

PROCESS FOR THE ENZYMATIC PREPARATION OF MACROLACTONE

This application is a continuation of application Ser. No. 08/119,229 filed Sep. 28, 1993, now abandoned, which was filed under 35 U.S.C § 371 as the national phase of PCT/FR92/00270, filed Mar. 26, 1992, published as WO92/17491 Oct. 15, 1992.

FIELD OF THE INVENTION

The present invention relates to the field of bioconversions. More particularly, it relates to an enzymatic process for preparing macrolactones of formula (1) from a macrolactone of formula (2) by means of a microorganism or from an acellular preparation derived from this microorganism.

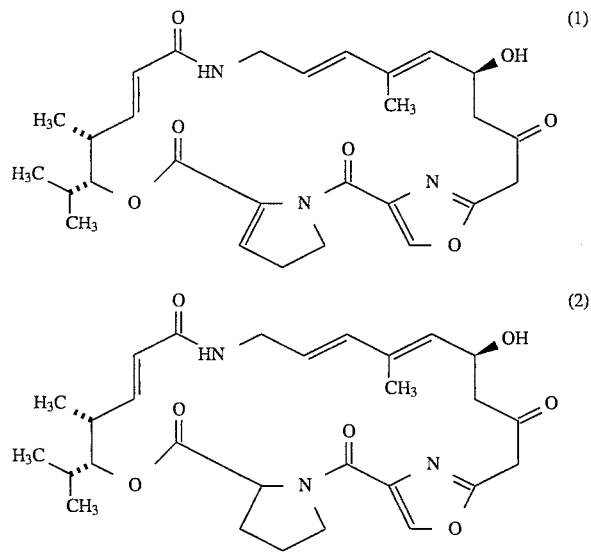

BACKGROUND OF THE INVENTION

The macrolactones of formula (1) and (2) are known under different names depending on their origins (table).

| Formula (1)    | Formula (2)    |
| -------------- | -------------- |
| pristinamycin PIIA | pristinamycin IIB |
| mikamycin A    |                |
| ostreogrycin A | ostreogrycin G |
| streptogramin A |               |
| synergistine A1 |               |
| vernamycin A   |                |
| virginiamycin M1 | virginiamycin M2 |

These molecules possess the general structure of polyunsaturated macrolactones which is found in antibiotics of the streptogramin family. These antibiotics indeed consist of the synergistic combination of a polyunsaturated macrolactone (component of group A) and a depsipeptide (component of group B). The mode of action and the antimicrobial activity of these antibiotics have been studied by various authors (Tanaka et al. Antibiotics vol. III p. 487, Springer Berlin, 1975; Vasquez et al. Antibiotics vol. III p. 521, Springer Berlin, 1975).

It emerges, in particular, from these various studies that a better synergy is obtained when only the macrolactone (1) is used as component of group A.

Moreover, one characteristic of the polyunsaturated macrolactones of the group A streptogramins is that of being barely soluble in an aqueous medium. This constitutes a major drawback in the pharmacological development of these molecules since their modes of administration are as a result very limited.

In order to overcome this disadvantage, a new generation of water-soluble semisynthetic derivatives has been developed (EP 135410; EP 191662; U.S. Pat. No. 4,775,753). The semisynthesis route used consists essentially of the addition of thiol to the unsaturated bond in 2-3 of the dehydroproline of macrolactones. However, given the structure of macrolactones, only the macrolactone (1) may be used in this semisynthesis route.

However, in current production systems, the macrolactones of formula (1) and (2) are synthesized simultaneously, and mixed with other streptogramin components.

It is therefore important to be able to increase the proportion of compound (1) relative to compound (2) in the production media.

It is also important to be able to upgrade the compounds (2) which are co-synthesized with the compound (1), and isolated from the fermentation broth at the same time.

Recently, Purvis et al. raised the possibility that the macrolactone (2) is an intermediate in the biosynthesis of the macrolactone (1) (J. Am. Chem. Soc., 1989, 111, 5931). However, nothing in this document describes or gives means for exploiting this reaction mechanism.

The Applicant has now shown that it is possible to convert, at high levels, the macrolactone (2) to macrolactone (1) by means of a microorganism or an acellular preparation derived from it.

BRIEF DESCRIPTION OF THE DRAWING

FIG. 1 is a graph showing the % conversion and titre of a culture over time using a microorganism to prepare the compound of formula (1) according to the present invention.

DESCRIPTION OF THE INVENTION

One subject of the present invention therefore consists of a process for preparing a compound of formula (1) characterized in that a compound of formula (2) is treated in the presence of a microorganism or an acellular preparation derived from this microorganism, capable of oxidizing the 2-3 bond of the D-proline of the polyunsaturated macrolactones of the group A streptogramins to dehydroproline.

The present invention may be used both in vitro and in vivo.

In vitro, it enables the macrolactone (1) to be synthesised from the macrolactone (2) isolated from the fermentation broth and which cannot be directly upgraded. The invention thus enables the macrolactone (2) to be converted at high levels to a substrate for semisynthesis reactions.

In vivo, it enables the level of the macrolactone (1) to be increased at the expense of the macrolactone (2) directly in the mixtures derived from the fermentation. It is indeed possible to introduce directly into the macrolactone production medium, a microorganism or an acellular preparation derived from it and possessing oxidative activity.

In a specific embodiment of the process of the invention, the microorganism or the acellular preparation derived from it is added directly to the macrolactone (2) production medium.

In a preferred embodiment of the invention, the compound (2) is treated by means of an acellular preparation.

The present invention thus enables the macrolactone (1) to be obtained in a simple manner, with levels of conversion of the compound (2) as high as 50% using whole microorganisms, and exceeding 90% when acellular preparations derived from these microorganisms are used.

The microorganisms which may be used in the present invention may be selected in several ways. In particular, the present invention describes a test enabling the microorganisms possessing the required enzymatic activity to be identified, and a quantitative estimation of this activity to be given. This test consists in carrying out the following steps:

incubating a culture of the microorganism studied or an acellular preparation derived from it in the presence of the labelled compound (2), removing samples of the culture medium over a period of time, separating the compounds (1) and (2), measuring the incorporated label in the compound (1), and determining the ratio of this label over the label introduced.

The ratio thus obtained enables the level of conversion to the compound (1), and therefore the level of enzymatic activity of the cultured microorganism to be obtained. It is understood that the selection of the microorganisms may be carried out by any other method enabling the presence of the enzymatic activity to be detected, and that the quantitative approach is optional.

Using this method of selection, various microorganisms, possessing a high enzymatic activity, have been identified.

Advantageously, in the process of the invention, the microorganism used is chosen from actinomycetes and fungi.

In particular, the streptogramin-producing microorganisms are generally suitable in the process of the invention. The same applies to the macrolactone (1)-producing microorganisms.

Among these microorganisms, the following strains may be mentioned more particularly:

Streptomyces pristinaespiralis

Streptomyces alborectus

Streptomyces diastaticus

Streptomyces graminofaciens

Streptomyces mitakaensis

Streptomyces loïdensis

Streptomyces olivaceus

Streptomyces ostréogriseus

Streptomyces virginiae, or

Micromonospora.

These microorganisms may be cultured under standard aerobic fermentation conditions. In particular, the nutrient medium generally consists of a carbon source, a nitrogen source and inorganic salts. As carbon source, sugars, oils, organic acids, dextrins, starches, glycerol and the like may be used in particular. As nitrogen source, amino acids, plant meals and extracts (malt, soya bean, cotton seeds, tomatoes, maize and the like), viscera, various hydrolysates (caseine, yeast and the like) and industrial biproducts such as "distillers' solubles" may be mentioned. As mineral source, sodium, potassium, ammonium or calcium chlorides, nitrates, carbonates, sulphates and phosphates or trace elements such as magnesium, iron, copper, zinc, manganese or cobalt may be used. Furthermore, using the selection test described above, the Applicant has shown that the desired enzymatic activity was expressed transiently by the various macroorganisms studied. Kinetics of expression of these enzymatic activity have been carried out which make it possible to define, for the microorganisms studied, the period of growth during which the expression of enzymatic activity is optimal. This therefore enables the yields of the process of the invention to be considerably improved.

In a preferred embodiment of the invention, a microorganism or an acellular preparation derived from a microorganism at the phase of optimal production of the enzymatic activity is used.

Still according to the present invention, it is possible, after a first selection stage, to use microorganisms possessing the enzymatic activity required to prepare derived strains exhibiting better catalytic potential and/or permitting a more efficient industrial exploitation. Such strains may be obtained using various tools for mutagenesis such as in particular:

physical agents: X-rays, ultra-violet rays, chemical agents: alkylating (ethyl methanesulfonate, nitrosoguanidine, NQO and the like), bifunctional alkylating or intercalating agents, systems for mutational insertion into DNA: transposons, integrative plasmids, phages or prophages and the like, or any other technique known to a person skilled in the art.

Still according to the present invention, it is possible to select within a population of cells possessing the required enzymatic activity, those which possess the best enzymatic activity and/or which give the best yields in the process of the invention.

In a specific embodiment of the process of the invention, a streptogramin-producing microorganism or one derived from a streptogramin producing microorganism is used.

Preferably, a microorganism chosen from the group comprising:

| | |
|---|---|
| S. pristinaespiralis | ATCC 25486 |
| S. ostreogriseus | ATCC 27455 |
| S. mitakaensis | ATCC 15297 |
| S. olivaceus | ATCC 12019 |
| S. loïdensis | ATCC 11415 | is used, and the microorganisms derived from them.

The enzymatic conversion reaction may be carried out either in the fermentation medium or in a buffered aqueous medium depending on whether an intact microorganism or an acellular preparation is used, and whether the procedure is carried out directly in the macrolactone production medium or using a compound (2) isolated from the fermentation broth.

When an acellular preparation is used, it may be advantageous to add to the reaction medium one or more enzymatic cofactors. In particular, the following cofactors make it possible to improve the reaction yields: NAD, NADP, NADH, NADPH, FAD and FMN.

The other reaction parameters are adjusted by a person skilled in the art according to the conditions used.

Another subject of the invention relates to the acellular preparations possessing an enzymatic activity capable of oxidizing the 2–3 bond of the D-proline of the polyunsaturated macrolactones of the group A streptogramins to hydroproline.

These acellular preparations may be obtained by various methods. In particular, they may be obtained by (a) disrupting the microorganisms described above and (b) optionally removing the cellular debris.

The disruption of the microorganisms may be carried out using various methods, and in particular physical, chemical or enzymatic methods. By way of example, there may be mentioned as physical methods, ultrasonication, grinding using glass beads or the French press and, as enzymatic method, lysozyme lysis.

The disruption may be carried out directly in the cell fermentation medium. However, the procedure is preferably carried out in a buffered aqueous medium. In this respect, it is possible to use an inorganic buffer (potassium phosphate and the like) or an organic buffer (Bis-Tris, Bis-Tris propane). Moreover, the reaction is advantageously carried out in the presence of a reducing agent. Dithiothreitol may be used in particular. Depending on the starting microorganism and the disruption conditions, the pH of the acellular preparations are adjusted to between pH 5.0 and pH 8.0, preferably between 6 and 7.

When desired, the cellular debris may be removed in various ways, the simplest consisting in centrifuging the suspension obtained after disruption and in dissolving the supernatant.

In order to check that the acellular preparation actually possesses the desired enzymatic activity or in order to select the most active acellular preparation, it is possible to use the above described test for selecting the microorganisms.

Moreover, in order to obtain acellular preparations with an optimal activity, it is possible, before carrying out the disruption stage, to determine the growth phase of the whole microorganisms corresponding to the maximum expression of the enzymatic activity. In particular, the kinetic curves obtained with the above described test may be used.

Preferably, in the process for producing the acellular preparations of the invention, the disruption step is carried out on microorganisms at the optimal production phase of the enzymatic activity.

EXAMPLES

Other subjects and advantages of the present invention will emerge from reading the following examples which should be considered as illustrative and non-restrictive.

Example 1

This example describes the preparation of the carbon 14-radiolabelled macrolactone (2).

750 µCi of [U-$^{14}$C]-L-proline are added to a *S.pristinaespiralis* culture, aged 17 hours, on a production medium in an Erlenmeyer flask (cf. Example 3). When the culture is aged 24 hours, it is harvested and the macrolactones (1) and (2) are extracted according to the following procedure:

55 ml of 0.1M phosphate buffer, pH 2.9 and 25 ml of acetonitrile are added to 30 ml of broth and the mixture is stirred and then centrifuged. After partial evaporation of the supernatant, it is extracted 3 times with one volume of dichloromethane and the 3 chloromethylene phases are combined and drained. The residue is taken up in chloroform containing 2% methanol and then injected onto a bare silica column and the compound (2) is eluted in chloroform containing 5% methanol. The compound (2) is purified by thin layer chromatography on bare silica using chloroform containing 8% methanol as eluent. It is repurified by HPLC on a Nucleosil C8 column (system described in Example 3) just before use.

As in the case of the acellular preparations (cf. FIG. 1), the time chosen for adding the labelled proline is important in order to obtain high specific activity values.

Example 2

This example describes a test permitting the selection of the microorganisms which may be used in the invention. It also illustrates how the level of enzymatic activity is dependant on the time of removing the cultures with respect to the onset of the production of the streptogramins.

The microorganism tested is a culture of *S.olivaceus* ATCC 12019 cultured under the conditions in Example 6. At various times, an acellular preparation is prepared from samples of this culture, in the following manner: 5 g of a centrifugation pellet, washed with a 0.1M phosphate buffer, pH 7.2 containing 10% v/v glycerol, are taken up in 10 ml of 100 mM Bis-Tris propane buffer, pH 6.8 containing 5 mM dithiothreitol and 0.2 mg/l of lysozyme. The suspension is incubated for 30 minutes at 27° C. and then centrifuged at 30,000 g for 30 minutes.

An acellular extract containing 50 µg of proteins (derived from the preparation obtained above) is incubated in a total volume of 500 µl in 50 mM Bis-tris propane buffer, pH 6.8, containing 0.25 µmol of NADH, 1 nmol of FMN and 3.65 µg of compound (2) labelled with carbon 14 according to Example 1 (that is 55 nCi), for 1 hour at 27° C. The reaction is stopped by the addition of 500 µl of acetonitrile and 500 µl of 0.1N hydrochloric acid.

After homogenization and centrifugation, 200 µl of the supernatant are injected onto a 15 cm 5 µ Nucleosil C8 analytical column eluted at 0.8 ml/min with a mixture of 34% $CH_3CN$ and 66% of 0.1M phosphate buffer, pH 2.9. The compounds (1) and (2) are assayed by spectrophotometric detection at 206 nm and by radiochemical detection.

The results obtained are presented in FIG. 1. They show that *S.olivaceus* possesses the desired enzymatic activity. They also show that this activity is expressed transiently, the optimal production phase being situated at around 21 hours of culture. Finally, they show that the activity occurs at the onset of the streptogramin production phase but that active acellular extracts may however be prepared before the start of streptogramin production.

Example 3

This example illustrates the process of the invention when an intact microorganism is used.

0.5 ml of a suspension of *Streptomyces pristinaespiralis* ATCC 25486 spores is added under sterile conditions to 40 ml of an inoculum medium in a 300-ml Erlenmeyer flask. The inoculum medium consists of 10 g/l of Corn steep; 15 g/l of sucrose; 10 g/l of $(NH_4)_2SO_4$; 1 g/l of $K_2HPO_4$; 3 g/l of NaCl; 0.2 g/l of $MgSO_4$-$7H_2O$; 1.25 g/l of $CaCO_3$. The pH is adjusted to 6.9 with sodium hydroxide before introducing the calcium carbonate. The Erlenmeyer flask is shaken for 46 hours 30 minutes at 27° C. on a rotary shaker at a speed of 325 r/min.

2.5 ml of the above culture, aged 46 hours 30 minutes, are added under sterile conditions to 30 ml of production medium in a 300-ml Erlenmeyer flask. The production medium consists of 25 g/l of soya bean meal; 7.5 g/l of starch; 22.5 g/l of glucose; 3.5 g/l of torula yeast; 0.5 g/l of zinc sulphate; and 6 g/l of calcium carbonate. The pH is adjusted to 6 with hydrochloric acid before adding the calcium carbonate. The Erlenmeyer flasks are shaken for 24 hours at 27° C. on a rotary shaker at a speed of 325 r/min. 10 mg/l of carbon 14-labelled compound (2) prepared according to Example 1 (that is 5.2 µCi of $^{14}$C per Erlenmeyer flask) are added to the Erlenmeyer flasks at times 0 and 17 hours 30 minutes. The reaction is stopped at time 24 hours by adding 2 volumes of a mixture of 34% $CH_3CN$ and 66% of 0.1M phosphate buffer, pH 2.9. After homogenisation and centrifugation, 200 µl of the supernatant are injected onto the 5 µ Nucleosil C8 column eluted with a mixture of 34% $CH_3CN$ and 66% of 0.1M phosphate buffer pH 2.9 in order to assay the compound (1) formed from the radioactive compound (2). The conversion levels of the compound (2) to the compound (1) are calculated from the amount of radioactivity found in the compound (1), corrected for the radioactivity introduced into the Erlenmeyer flask (plugged Erlenmeyer flasks with air circulation: air flow rate 1 l/min).

The results are presented below:

| Time of addition of the compound (2) | Conversion level | Residual Compound (2) (%) |
|---|---|---|
| 0 | 36 | 11 |
| 17 hours 30 minutes | 45 | 29 |

Example 4

The procedure described in Example 3 is repeated using a suspension of *Streptomyces ostreogriseus* ATCC 27455 spores. The results obtained are presented below:

| Time of addition of the compound (2) | Conversion level | Residual Compound (2) (%) |
|---|---|---|
| 17 hours 30 minutes | 44 | 19 |

Example 5

The procedure described in Example 3 is repeated using a suspension of *Streptomyces mitakensis* ATCC 15297 spores. The results obtained are presented below:

| Time of addition of the compound (2) | Conversion level | Residual Compound (2) (%) |
|---|---|---|
| 0 | 34 | 10 |
| 17 hours 30 minutes | 43 | 18 |

Example 6

The procedure described in Example 3 is repeated using a suspension of *Streptomyces olivaceus* ATCC 12019 spores. The results obtained are presented below:

| Time of addition of the compound (2) | Conversion level | Residual Compound (2) (%) |
|---|---|---|
| 0 | 39 | 14 |
| 17 hours 30 minutes | 50 | 16 |

Example 7

The procedure described in Example 3 is repeated using a suspension of *Streptomyces loïdensis* ATCC 11415 spores. The results obtained are presented below:

| Time of addition of the compound (2) | Conversion level | Residual Compound (2) (%) |
|---|---|---|
| 0 | 46 | 11 |
| 17 hours 30 minutes | 53 | 16 |

Example 8

5 g of a centrifugation pellet, washed with a 0.1M phosphate buffer pH 7.2 containing 10% v/v of glycerol, of a *S.olivaceus* ATCC 12019 culture, aged 22 hours 30 minutes, obtained under the conditions in Example 6, are taken up in 10 ml of 50 mM Bis-Tris propane buffer pH 6.8.

500 µl of this preparation are incubated with 3.65 µg of the compound (2) labelled with carbon 14 according to Example 1 (55 nCi), for 2 hours at 27° C. 1 ml of a mixture of 66% of 0.1M phosphate buffer pH 2.9 and 34% acetonitrile are added at the end of the incubation. After homogenization and centrifugation, 200 µl of the supernatant are analysed by HPLC (Example 3) in order to assay the radioactive compound (1).

The level of conversion of the compound (2) to the compound (1) is 30%.

Example 9

5 g of a centrifugation pellet, washed with a 0.1M phosphate buffer pH 7.2 containing 10% v/v of glycerol, of a *S.loïdensis* ATCC 11415 culture, aged 17 hours 30 minutes, obtained under the conditions in Example 7, are taken up in 10 ml of 50 mM Bis-Tris propane buffer pH 6.8.

500 µl of this preparation are incubated with 3.65 µg of the compound (2) labelled with carbon 14 according to Example 1 (55 nCi), for 2 hours at 27° C. 1 ml of a mixture of 66% of 0.1M phosphate buffer pH 2.9 and 34% acetonitrile are added at the end of the incubation. After homogenization and centrifugation, 200 µl of the supernatant are analysed by HPLC (Example 3) in order to assay the radioactive compound (1).

The level of conversion of the compound (2) to the compound (1) is 53%.

Example 10

5 g of a centrifugation pellet, washed with a 0.1M phosphate buffer pH 7.2 containing 10% v/v of glycerol, of a *S.pristinaespiralis* culture, aged 19 hours, obtained under the conditions in Example 3, are taken up in 10 ml of 100 mM Bis-Tris propane buffer pH 6.8 containing 5 mM dithiothreitol and 0.2 mg/l of lysozyme. The suspension is incubated for 30 minutes at 27° C. and then centrifuged at 30,000 g for 30 minutes. The supernatant constitutes the acellular preparation.

In a first experiment, 207 µl of this preparation (1 mg of proteins) are incubated in a total volume of 500 µl in 5 mM Bis-Tris propane buffer pH 6.8 containing 0.25 µmol of NADH; 1 nmol of FMN and 3.65 µg of compound (2) labelled with carbon 14 according to Example 1 (55 nCi), for 1 hour at 27° C.

9

In a second experiment, 414 µl of the acellular preparation (2 mg of proteins) are used.

The reactions are stopped by the addition of 500 µl of CH₃CN and 500 µl of 0.1N hydrochloric acid. After homogenization and centrifugation, 200 µl of the supernatant are injected onto a 5 µ Nucleosil C8 column, eluted with a mixture of 34% CH₃CN and 66% of 0.1M phosphate buffer pH 2.9 in order to assay the compound (1) formed from the radioactive compound (2). The levels of conversion of the compound (2) to the compound (1) are calculated as in Example 3.

The results obtained are presented below:

| Suspension volume | Conversion level | Residual Compound (2) (%) |
|---|---|---|
| 207 µl | 63 | 29 |
| 414 µl | 76 | 17 |

Example 11

5 g of a centrifugation pellet, washed with a 0.1M phosphate buffer pH 7.2 containing 10% v/v of glycerol, of a *S.olivaceus* ATCC 12019 culture, aged 21 hours, obtained under the conditions in Example 6, are taken up in 10 ml of 100 mM Bis-Tris propane buffer pH 6.8 containing 5 mM dithiothreitol and 0.2 mg/l of lysozyme. The suspension is incubated for 30 minutes at 27° C. and then centrifuged at 30,000 g for 30 minutes. The supernatant constitutes the acellular preparation.

An acellular extract (22 µl of the above preparation) containing 0.1 mg of proteins is incubated in a total volume of 500 µl in 50 mM Bis-Tris propane buffer pH 6.8 containing 0.25 µmol of NADH; 1 nmol of FMN and 3.65 µg of the compound (2) labelled with carbon 14 according to Example 1 (55 nCi), for 1 hour at 27° C.

The reaction is stopped by the addition of 500 µl of CH₃CN and 500 µl of 0.1N hydrochloric acid. After homogenization and centrifugation, 200 µl of the supernatant are analysed by HPLC in order to assay the radioactive compound (1).

The level of conversion of the compound (2) to the compound (1) is 93%.

Example 12

5 g of a centrifugation pellet, washed with a 0.1M phosphate buffer pH 7.2 containing 10% v/v of glycerol, of a *S.loidensis* ATCC 11415 culture, aged 17 hours 30 minutes, obtained under the conditions in Example 7, are taken up in 10 ml of 100 mM Bis-Tris propane buffer pH 6.8 containing 5 mM of dithiothreitol and 0.2 mg/l of lysozyme. The suspension is incubated for 30 minutes at 27° C. and then centrifuged at 30,000 g for 30 minutes. The supernatant constitutes the acellular preparation.

79 µl of this acellular preparation, that is 0.2 mg of proteins, are incubated in a total volume of 500 µl in 50 mM Bis-Tris propane buffer pH 6.8 containing 0.25 µmol of NADH; 1 nmol of FMN and 3.65 µg of the compound (2) labelled with carbon 14 according to Example 1 (55 nCi) for 1 hour at 27° C.

The reaction is stopped by the addition of 500 µl of CH₃CN and 500 µl of 0.1N hydrochloric acid. After homogenization and centrifugation, 200 µl of the supernatant are analysed by HPLC in order to assay the radioactive compound (1).

The level of conversion of the compound (2) to the compound (1) 92%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for preparing a compound of formula (1),

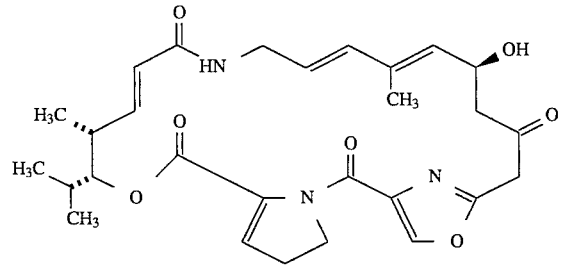

said process comprising:

(a) incubating a compound of formula (2)

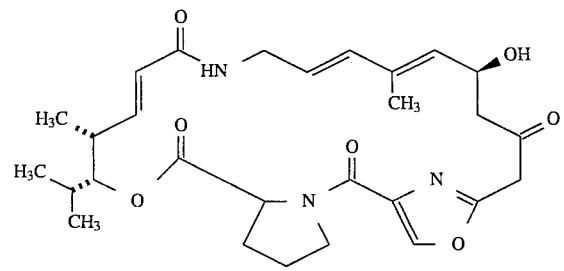

in an aerobic culture medium containing a microorganism, wherein said microorganism is selected from the group consisting of *Streptomyces pristinaespiralis* ATCC 25486, *Streptomyces mitakaensis* ATCC 15297, *Streptomyces ostreogriseus* ATCC 27455, *Streptomyces olivaceus* ATCC 12019, and *Streptomyces loidensis* ATCC 11415;

wherein said incubating with said microorganism results in a bioconversion of the compound of formula (2) of about 50%, wherein said microorganism oxidizes the 2–3 bond of D-proline of polyunsaturated macrolactones of group A streptogramins to dehydroproline; and (b) recovering the compound of formula (1).

2. The process of claim 1, wherein said microorganism is added directly to the aerobic culture medium.

3. The process of claim 1, wherein said aerobic culture medium comprises a buffered aqueous medium.

4. A process for preparing a compound of formula (1),

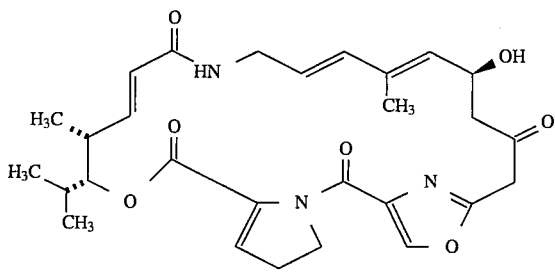

said process comprising:

(a) incubating a compound of formula (2)

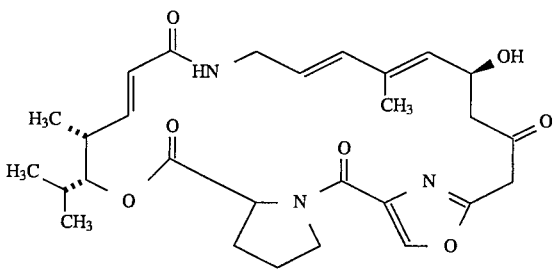

in an aerobic culture medium containing an acellular extract derived from microorganism, wherein said microorganism is selected from the group consisting of *Streptomyces pristinaespiralis* ATCC 25486, *Streptomyces mitakaensis* ATCC 15297, *Streptomyces ostreogriseus* ATCC 27455, *Streptomyces olivaceus* ATCC 12019, and *Streptomyces loidensis* ATCC 11415, wherein said acellular preparation is obtained by disrupting said microorganism and collecting the resulting supernatant, wherein said incubating with said acellular preparation results in a yield of about 90%, wherein said acellular preparation oxidizes the 2–3 bond of D-proline of polyunsaturated macrolactones of group A streptogramins to dehydroproline; and (b) recovering the compound of formula (1).

5. The process of claim 1, wherein said acellular preparation is added directly to the aerobic culture medium.

6. The process of claim 1, wherein said aerobic culture medium comprises a buffered aqueous medium.

7. The process of claim 1, wherein said incubation is carried out in the presence of at least one enzymatic cofactor, wherein said cofactor is selected from the group consisting of NAD, NADP, NADH, NADPH, FAD, and FMN.

8. The process of claim 1, wherein said incubation is carried out in the presence of at least one enzymatic cofactor, wherein said cofactor is selected from the group consisting of NADH and FMN.

* * * * *